(12) United States Patent
Sasaki et al.

(10) Patent No.: US 10,357,300 B2
(45) Date of Patent: Jul. 23, 2019

(54) DISPENSING SYSTEM AND METHOD

(71) Applicant: Medtronic Holding Company Sàrl, Tolochenaz (CH)

(72) Inventors: Neil Sasaki, San Jose, CA (US); Amy L. Arthur, San Jose, CA (US); Samuel V. Bolosan, San Jose, CA (US)

(73) Assignee: Medtronic Holding Company Sárl, Tolochenaz (CH)

( * ) Notice: Subject to any disclaimer, the term of this patent is extended or adjusted under 35 U.S.C. 154(b) by 216 days.

(21) Appl. No.: 15/612,063

(22) Filed: Jun. 2, 2017

(65) Prior Publication Data

US 2017/0348036 A1 Dec. 7, 2017

Related U.S. Application Data

(60) Provisional application No. 62/345,404, filed on Jun. 3, 2016.

(51) Int. Cl.
*A61B 17/88* (2006.01)
*A61B 90/00* (2016.01)
(Continued)

(52) U.S. Cl.
CPC ...... *A61B 17/8833* (2013.01); *A61B 17/8816* (2013.01); *A61B 17/8822* (2013.01);
(Continued)

(58) Field of Classification Search
CPC ............ A61B 17/8833; A61B 17/8816; A61B 17/8822
See application file for complete search history.

(56) References Cited

U.S. PATENT DOCUMENTS 8,439,929 B1 * 5/2013 Sharratt ................ A61F 2/4601
604/122
2001/0008968 A1 * 7/2001 Overes ............... A61B 17/8822
606/93
(Continued)

FOREIGN PATENT DOCUMENTS

EP 2269541 A1 1/2011
EP 2446973 A2 5/2012

OTHER PUBLICATIONS

PCT/IB2017/000761—International Search Report, Written Opinion of the International Searching Authority EPO, dated Nov. 27, 2017.
(Continued)

*Primary Examiner* — Christian A Sevilla

(57) ABSTRACT

A delivery system is provided that includes a device having a body extending along a longitudinal axis between proximal and distal ends. The body includes a proximal chamber, a distal chamber and a wall between the chambers. The body includes a first port in communication with the proximal chamber and a second port in communication with the distal chamber. A shaft is movably positioned within the body. The shaft extends through the wall and includes a proximal plunger positioned within the proximal chamber and a distal plunger positioned within the distal chamber. Pressure introduced through an opening in the proximal end moves the shaft such that the proximal plunger moves a fluid within the proximal chamber out of the first port and the distal plunger moves a fluid within the distal chamber out of the second port to simultaneously actuate a bone filler dispenser. Systems and methods are also provided.

20 Claims, 13 Drawing Sheets

(51) Int. Cl.
  *B01F 15/02* (2006.01)
  *B65D 81/32* (2006.01)
  *B01F 3/08* (2006.01)
  *B01F 3/10* (2006.01)
  *B01F 5/06* (2006.01)
  *B01F 15/04* (2006.01)
  *B05C 17/005* (2006.01)
  *B05C 17/015* (2006.01)

(52) U.S. Cl.
  CPC ........ *A61B 17/8825* (2013.01); *B01F 3/0861* (2013.01); *B01F 3/10* (2013.01); *B01F 5/0614* (2013.01); *B01F 5/0615* (2013.01); *B01F 15/0223* (2013.01); *B01F 15/0237* (2013.01); *B01F 15/0416* (2013.01); *B05C 17/00559* (2013.01); *B05C 17/015* (2013.01); *B65D 81/325* (2013.01); *A61B 2017/8838* (2013.01); *A61B 2090/3966* (2016.02); *B01F 2215/0029* (2013.01)

(56) References Cited

U.S. PATENT DOCUMENTS

| | | | |
|---|---|---|---|
| 2002/0049449 A1* | 4/2002 | Bhatnagar | A61B 17/3472 606/94 |
| 2007/0228076 A1 | 10/2007 | Horner et al. | |
| 2008/0272149 A1* | 11/2008 | Virnelson | B05C 17/00553 222/137 |
| 2009/0171361 A1 | 7/2009 | Melsheimer et al. | |
| 2011/0106054 A1 | 5/2011 | Osborne et al. | |
| 2013/0013007 A1* | 1/2013 | Broome | A61B 17/8811 606/86 R |
| 2018/0125558 A1* | 5/2018 | Flores | A61B 17/8833 |

OTHER PUBLICATIONS

International Search Report and Written Opinion of the International Searching Authority, European Patent Office, PCT/IB2017/000761, dated Dec. 13, 2018.

* cited by examiner

DISPENSING SYSTEM AND METHOD

TECHNICAL FIELD

The present disclosure generally relates to medical devices for bone repair, and more particularly to a medical system and method for mixing and dispensing bone cement or other materials.

BACKGROUND

Many medical procedures employ medical grade cement in connection with the restoration and strengthening of bone structures. During such procedures, cement is typically dispensed to a bone to fill in voids or spaces in the bone or between medical devices or implants attached to or embedded within the bone. These dispensing devices may include systems as simple as syringes and as complex as electronically controlled valves.

Due to the medical nature of some procedures, the amount and placement of the fluids, such as, cement, need to be supervised carefully. Despite the simplicity or complexity of the dispensing system, control over when, where and how much cement is dispensed is of concern. Currently, there is a need for an easier bone cement mixer and dispensing tool that would permit for fewer steps or less complicated steps in a mixing and dispensing process. This disclosure describes improvements over these prior technologies in providing improved systems for dispensing fluids.

SUMMARY

In one embodiment, a delivery system is provided. The delivery system includes a device having a body extending along a longitudinal axis between opposite proximal and distal ends. The body includes a proximal chamber, a distal chamber and a wall between the chambers. The body includes a first port in communication with the proximal chamber and a second port in communication with the distal chamber. A shaft is movably positioned within the body. The shaft extending through the wall and comprising a proximal plunger positioned within the proximal chamber and a distal plunger positioned within the distal chamber. Wherein pressure introduced through an opening in the proximal end moves the shaft such that the proximal plunger moves a fluid within the proximal chamber out of the first port and the distal plunger moves a fluid within the distal chamber out of the second port to simultaneously actuate a bone filler dispenser. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
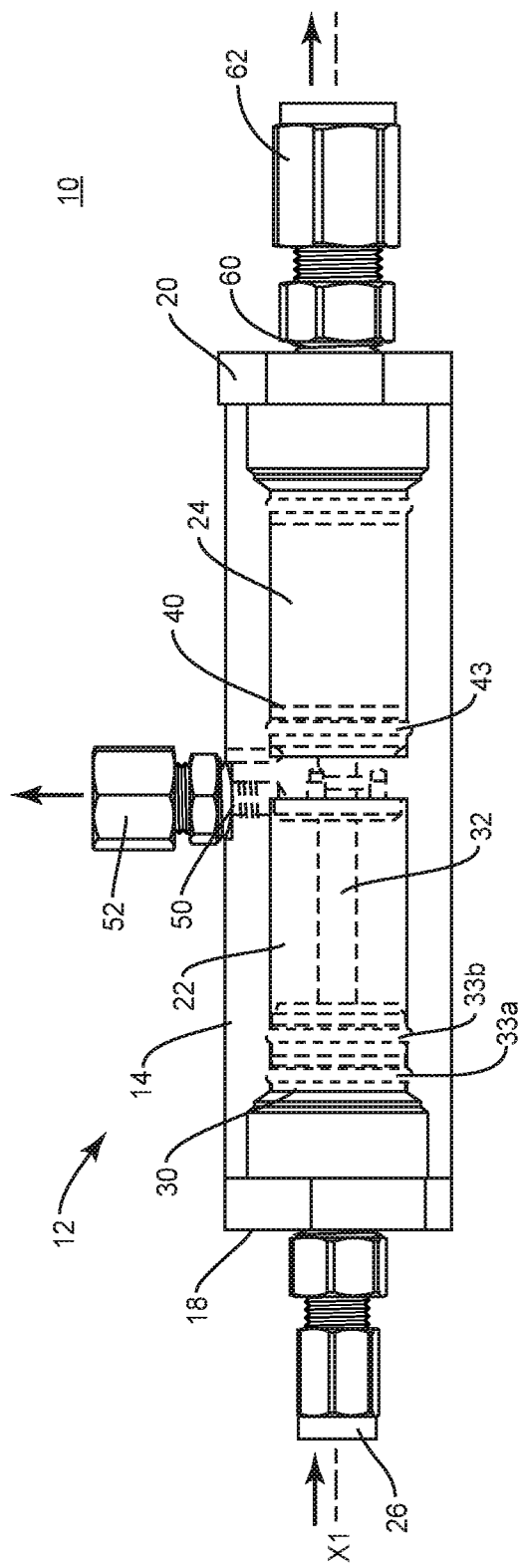
FIG. 1 is a cross-sectional view of components of a delivery system in accordance with the principles of the present disclosure.
Figure 2:
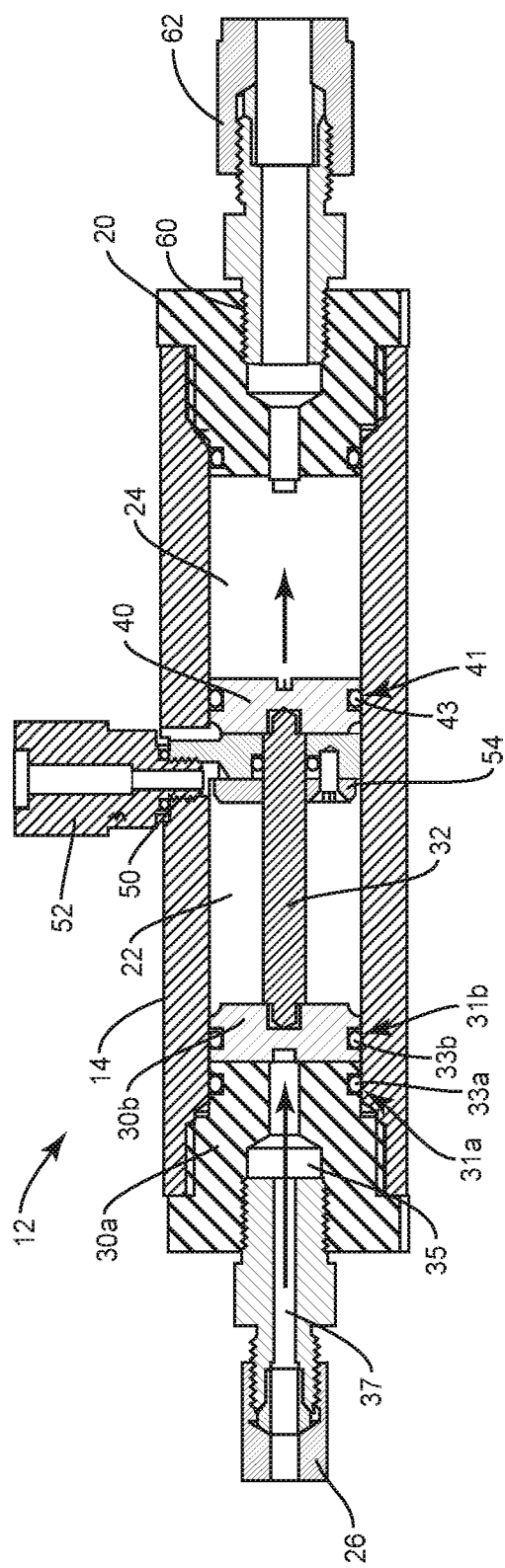
FIG. 2 is a cross-sectional view of components of a delivery system in accordance with the principles of the present disclosure.
Figure 3:
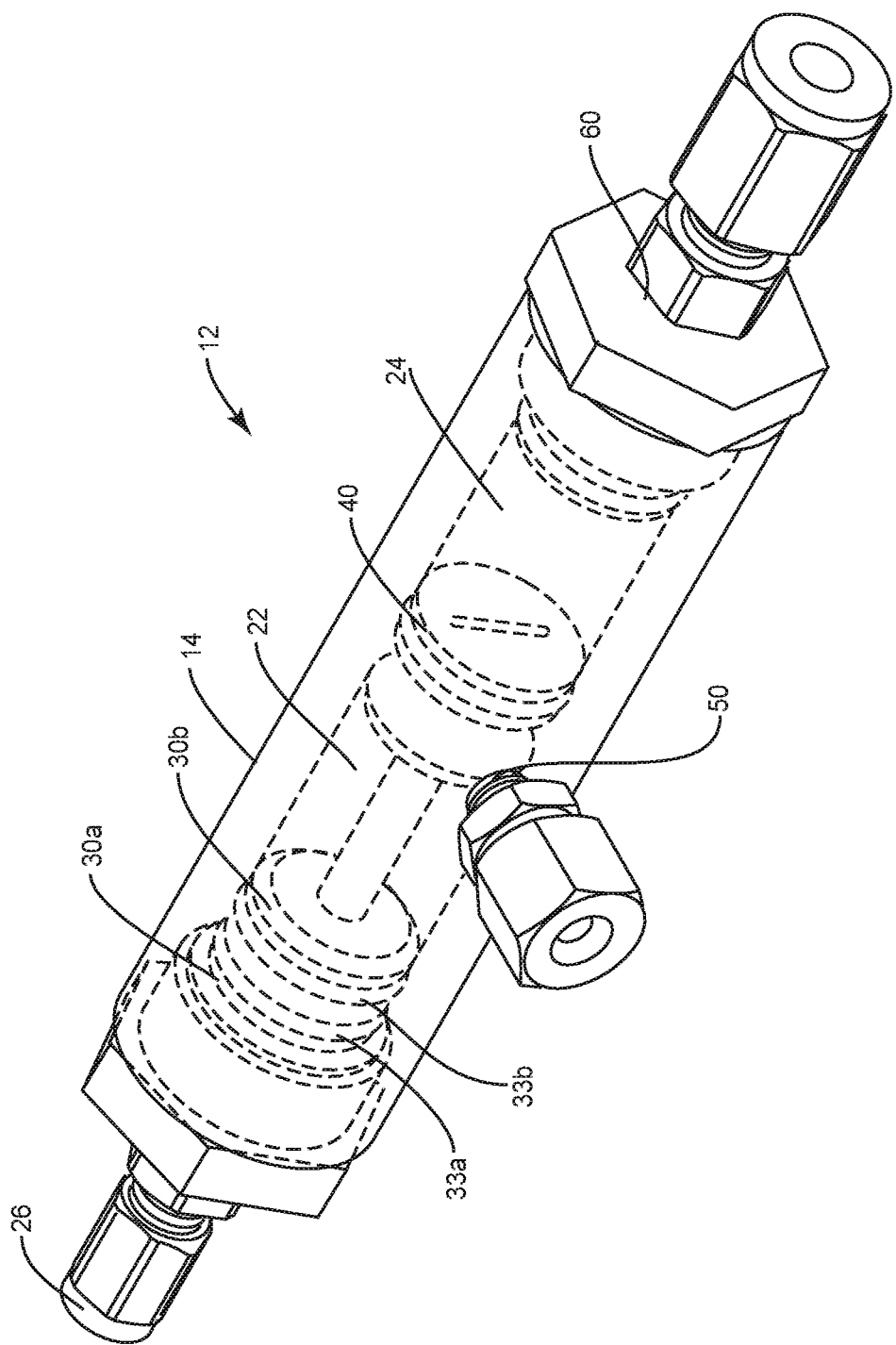
FIG. 3 is a cross-sectional view of components of a delivery system in accordance with the principles of the present disclosure.
Figure 3A:
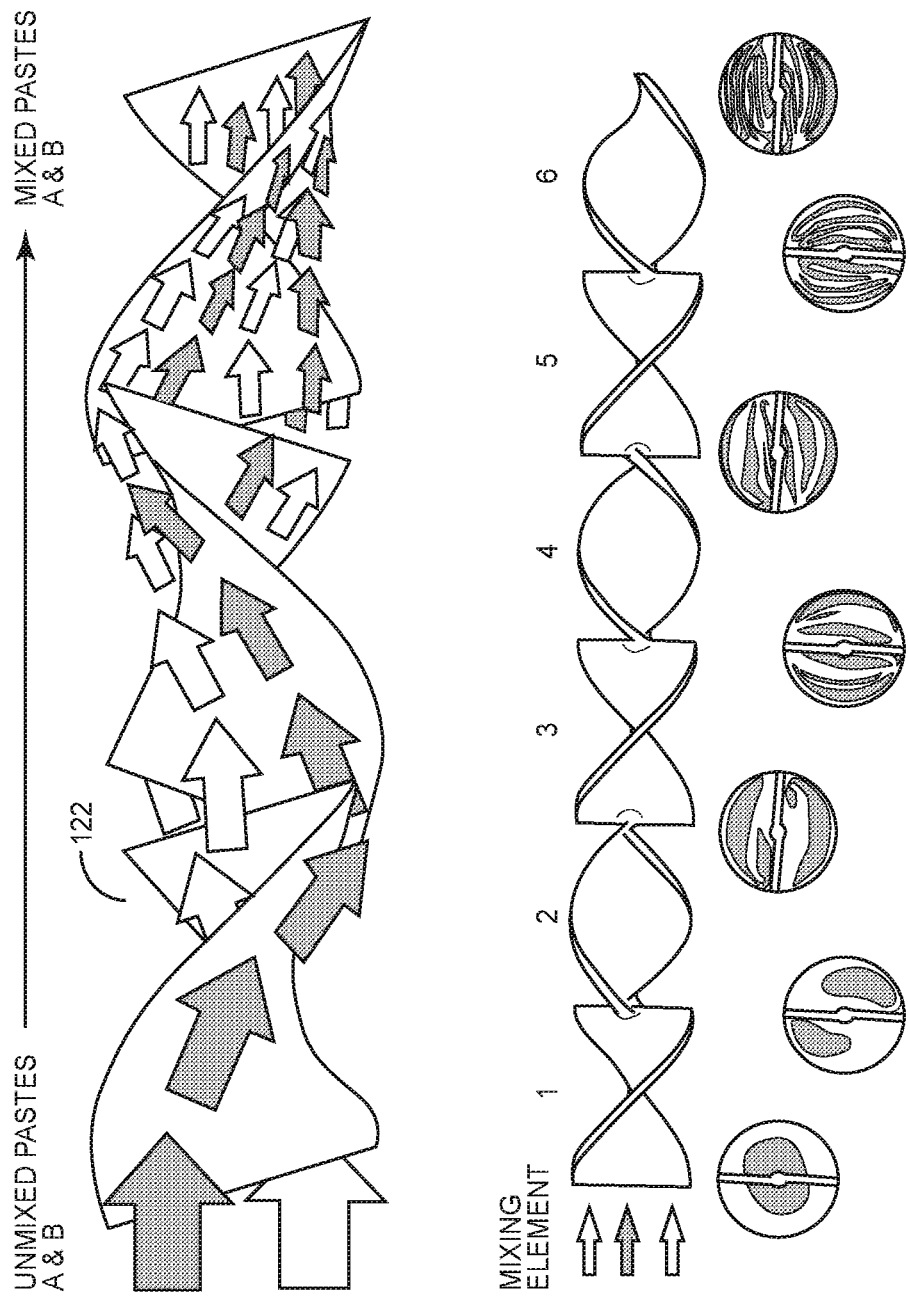
FIG. 3a is a perspective view of components of a delivery system in accordance with the principles of the present disclosure.

The exemplary embodiments of a delivery system and related methods are discussed in terms of medical devices for the treatment of skeletal injuries, disorders and repairs and more particularly, in terms of a mixing and dispensing gun and method for bone repair. In some embodiments, the system and method may be employed in applications such as correction of cracks, fissures, voids, e.g., due to osteoporosis or other diseases or injuries. In addition, the system and method may be employed with the placement of support structures or devices attached to or embedded within bone. For example, such structures may include pins, screws, replacement joints (e.g., of the hip, knee, shoulder), etc.

In some embodiments, the delivery system includes a device, such as, for example, a master cylinder including two chambers. In some embodiments, the chambers are filled with a fluid material. In some embodiments, the device includes chambers disposed in series so as to synchronize expulsion of the fluid to actuate a bone filler dispenser. In some embodiments, the series configuration facilitates control of the mixture ratio. In some embodiments, the device is configured to facilitate use with low pressure applications where space is readily available. In some embodiments, the device is configured to provide for remote delivery (i.e. out of floro) and high pressure delivery. In some embodiments, the device provides a minimal footprint and a less cumbersome configuration. In some embodiments, the device maximizes the use of hydraulic pressures but utilizing a dual circuit hydraulic cylinder delivery system. In some embodiments, the device utilizes hydraulic pressure to simultaneously apply pressure on two plungers that are mechanically connected in series. In some embodiments, as the pressure is applied to a proximal plunger, force is applied to a distal plunger.

In some embodiments, the device allows for a single hydraulic force to act on two plungers, maximizing output force while minimizing input force. In some embodiments, the device allows for a single hydraulic signal to dispense cement at a 1:1 ratio (or any other ratio) which is critical to ensure proper mixing of materials.

In some embodiments, the master cylinder includes a hydraulic port. In some embodiments, the mixer includes a first and a second chamber. In some embodiments, the device is configured for connection with a hydraulic source and/or inflation syringe. In some embodiments, the first chamber includes a plunger and the second chamber includes a plunger. In some embodiments, the first chamber includes a smaller volume due to disposal of a plunger shaft therein. In some embodiments, the second chamber includes a smaller diameter to account for volume differential. In some embodiments, the first chamber includes a first material. In some embodiments, the second chamber includes a second material. In some embodiments, the first chamber is configured with a port to expel the first material to a static mixer. In some embodiments, the second chamber includes a port to expel the second material to the static mixer.

In some embodiments, the device includes a rod disposed with the first chamber configured with a diameter equal to the CDS cartridge. In some embodiments, the first chamber includes a seal configured to resist and/or prevent material from mixing within the chamber. In some embodiments, the second chamber includes an air vent. In some embodiments, the ports are configured for connection with tubing such as, for example, ¼ inch tubing. In some embodiments, the ports include universal end caps for connection with the tubing. In some embodiments, the plunger in the first chamber includes a slot for engagement with an instrument such as, for example, a driver.

In some embodiments, the device expels the materials through the ports to a static mixer. In some embodiments, the static mixer includes a mixing blade. In some embodiments, the ports a disposed perpendicular to an axis of the mixer. In some embodiments, the ports are disposed transverse to an axis of the mixer. In some embodiments, the static mixer is connected with a cannula for disposal with a surgical site. In some embodiments, the device is configured for connection with a dual chamber plunger. In some embodiments, the dual chamber plunger is connected with the static mixer.

In some embodiments, one or all of the components of the surgical system may be disposable, peel-pack, pre-packed sterile devices. One or all of the components of the surgical system may be reusable. The surgical system may be configured as a kit with multiple sized and configured components.

In some embodiments, the present disclosure may be employed to treat or repair bone injuries or disorders such as, for example, osteoporosis, joint replacement, fracture repairs, bone breaks, etc. In some embodiments, the present disclosure may be employed with other osteal and bone related applications, including those associated with diagnostics and therapeutics, such as the delivery of a therapeutic agents to a site for treatment or the delivery of radio opaque markers for tracking fluid once it is released into a patient. In some embodiments, the disclosed surgical system and methods may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a mixer gun system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-19, there are illustrated components of a surgical system, such as, for example, a delivery system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 is employed, for example, with an open, mini-open or minimally invasive surgical technique to fill voids, provide patches, attach prosthetic devices, etc., or any other bone related repairs. System 10 includes a device, such as, for example, a master cylinder 12 configured to simultaneously actuate translation of plungers in a bone filling dispenser 100, as described herein. In some embodiments, the plungers are actuated to translate at an equal rate. In some embodiments, utilization of cylinder 12 facilitates the utilization of a hydraulic force applied to actuate the plungers, as described herein.

Cylinder 12 includes a body 14. Body 14 extends between a proximal end 18 and a distal end 20 defining a longitudinal axis X1. Body 14 includes a barrel that encloses a chamber 22 and a chamber 24. In some embodiments, body 14 may have cross section configurations, such as, for example, oval, cylindrical, triangular, square, polygonal, irregular, uniform, non-uniform, offset, staggered, undulating, arcuate, variable and/or tapered. In some embodiments, a wall of barrel 14 can be flexible, elastic, semi-rigid or rigid.

Chambers 22, 24 are disposed in a series configuration, as described herein. Chamber 22 includes a port 26 configured for connection with an actuator, such as, for example, a hydraulic pressure source. Port 26 defines an opening and is configured for connection with tubing configured for attachment with the pressure source. In some embodiments, port 26 includes a taper, nozzle, valve and/or luer lock connection for connecting with the tubing. In some embodiments, port 26 includes a pressure fit, friction fit or threaded connection for connecting with the tubing. In some embodiments, port 26 is integrally connected or monolithically formed with the tubing. In some embodiments, the tubing includes ¾ inch tubing.

Chamber 22 includes a pneumatic material, such as, for example a fluid. In some embodiments, the fluid may be, such as, for example, water, oil or saline. Chamber 22 includes a plunger 30 configured to actuate movement of the fluid within chamber 22. The pressure source applies a force to plunger 30 to actuate translation of plunger 30 within chamber 22. Plunger 30 includes a first part 30a and a second part 30b that is movable relative to first part 30a. First part 30a includes a channel 35 that is in communication with a lumen 37 of port 26. As a material, such as, for example, air or a liquid moves through lumen 37 and into channel 35, the material creates pressure within channel 35, which causes second part 30b to translate relative to first part 30a along axis X1. Second part 30b of plunger 30 includes a shaft 32 configured for engagement with a plunger 40 to actuate translation of plunger 40 within chamber 24. Plunger 30 is configured to actuate movement of the fluid within chamber 22. First part 30a of plunger 30 includes a recess 31a having a plunger seal 33a disposed therein that slidably engages the wall of chamber 22. Likewise, second part 30b of plunger 30 includes a recess 31b having a plunger seal 33b disposed therein that slidably engages the wall of chamber such that second part 30b is movably disposed with body 14. Plunger seal 33a and/or plunger seal 33b is/are configured to resist and/or prevent the fluid within chamber 22 from exiting chamber 22.

Plunger seal 33b is configured to translate within chamber 22 and contact the fluid within chamber 22. Second part 30b of plunger 30 translates along axis X1 relative to body 14 between an initial orientation and a fully or entirely expelled orientation. In the initial orientation, second part 30b of plunger 30 is disposed adjacent the fluid within chamber 22. Second part 30b of plunger 30 translates such that plunger seal 33b applies a force to the fluid within chamber 22. The force applied by plunger seal 33b causes the fluid to be moved through an opening 50. In some embodiments, opening 50 is disposed perpendicular relative to axis X1. Compression of the first material causes the fluid within chamber 22 to flow from chamber 22 through opening 50. Movement of the fluid from chamber 22 causes a plunger in bone filling dispenser 100 to be actuated, as described herein. In some embodiments, chamber 22 includes an O-ring retainer 54. O-ring retainer 54 is configured to facilitate movement of the fluid within chamber 22 through opening 50.

Chamber 24 includes the second material. In some embodiments, the second material includes a pneumatic material, such as, for example a fluid. In some embodiments, the fluid may be, such as, for example, water, oil or saline. Plunger 40 is actuated by second part 30b of plunger 30 such that plungers 30, 40 expel the fluid from chambers 22, 24 simultaneously from cylinder 12. Disposal of chambers 22, 24 in the series configuration allows the force applied to second part 30b of plunger 30 to translate plunger 40. In some embodiments, this configuration utilizes a reduced and/or lower hydraulic force to expel the fluid. The force applied to plungers, 30, 40 is configured to simultaneously expel the fluid from chambers 22, 24.

Plunger 40 is configured to actuate movement of the fluid within chamber 24. Plunger 40 includes a recess 41 having a plunger seal 43 disposed therein that slidably engages the wall of chamber 24 such that plunger 40 is movably disposed with body 14. Plunger seal 43 is configured to resist and/or prevent the fluid within chamber 24 from exiting chamber 24.

Figure 4:
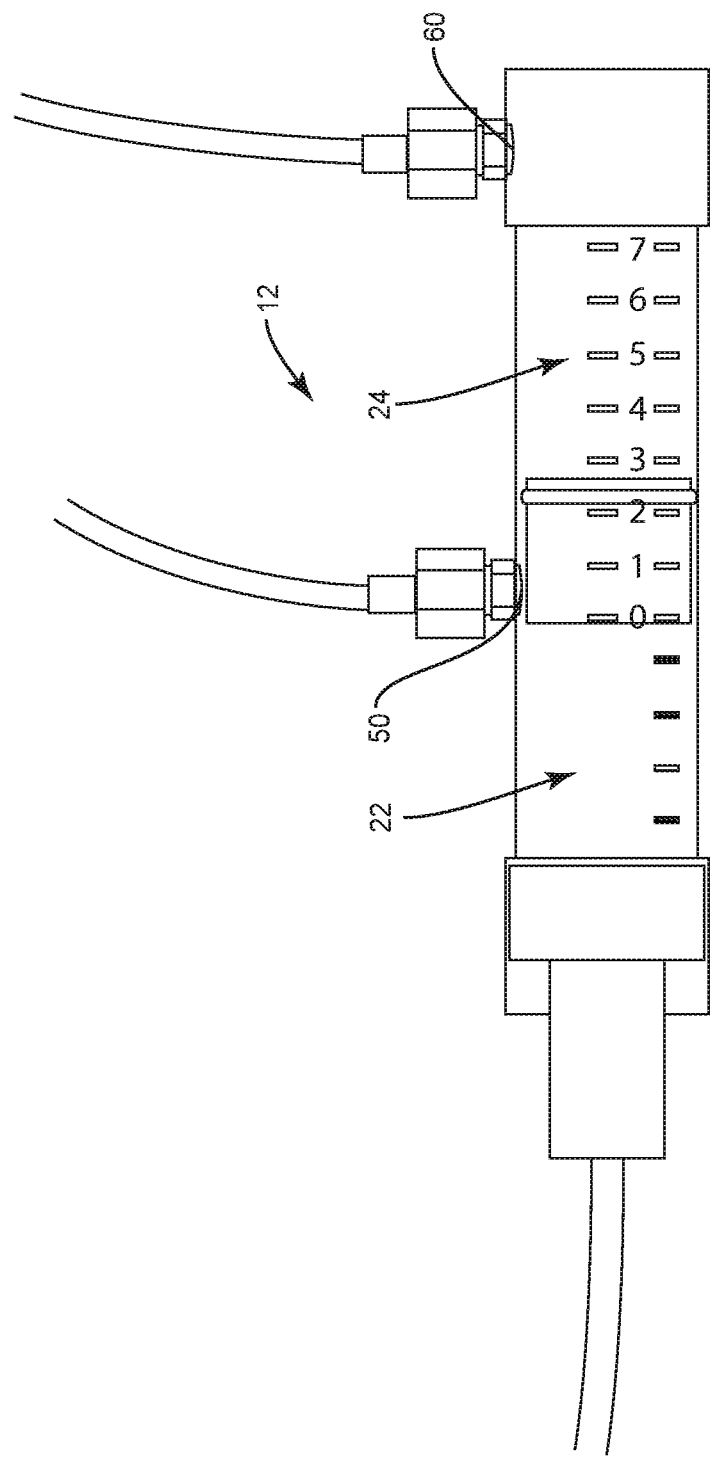
FIG. 4 is a perspective view of components of a delivery system in accordance with the principles of the present disclosure.
Figure 5:
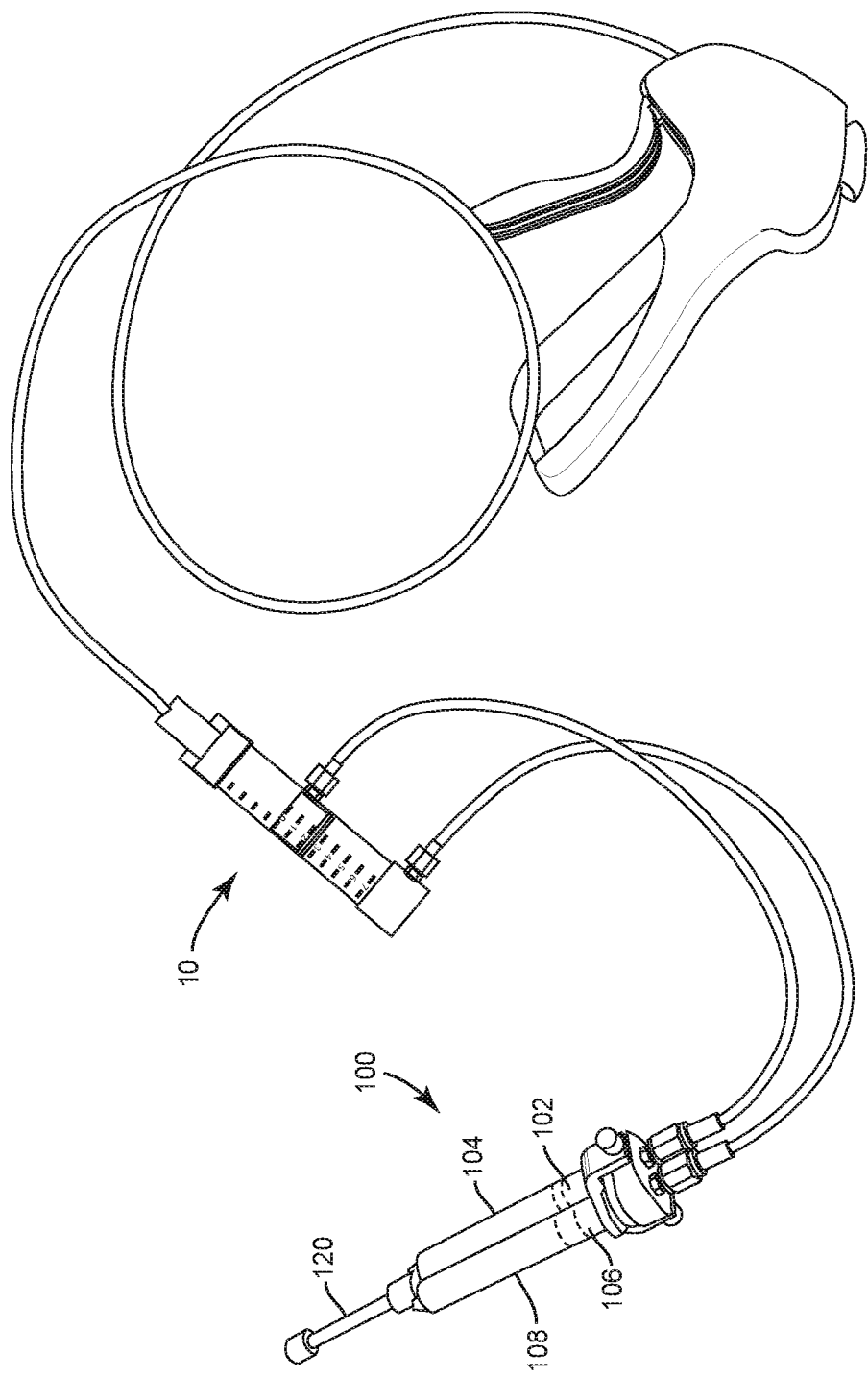
FIG. 5 is a perspective view of components of a delivery system in accordance with the principles of the present disclosure.
Figure 6:
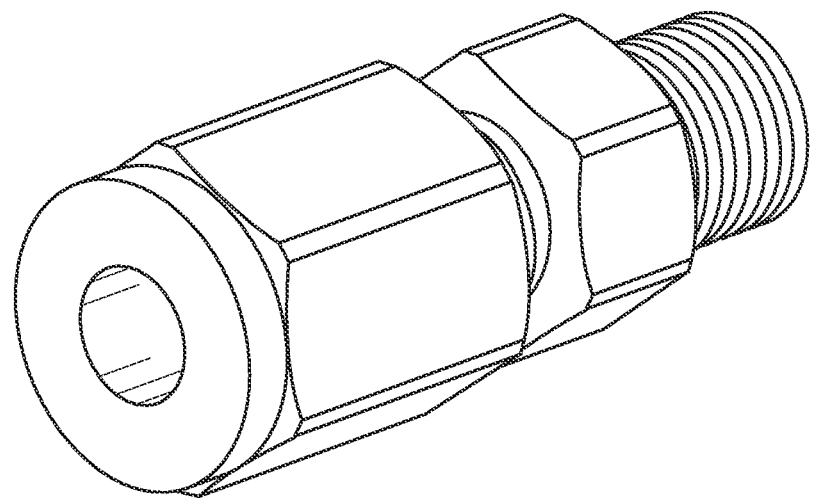
FIG. 6 is a perspective view of a component of a delivery system in accordance with the principles of the present disclosure.
Figure 7:
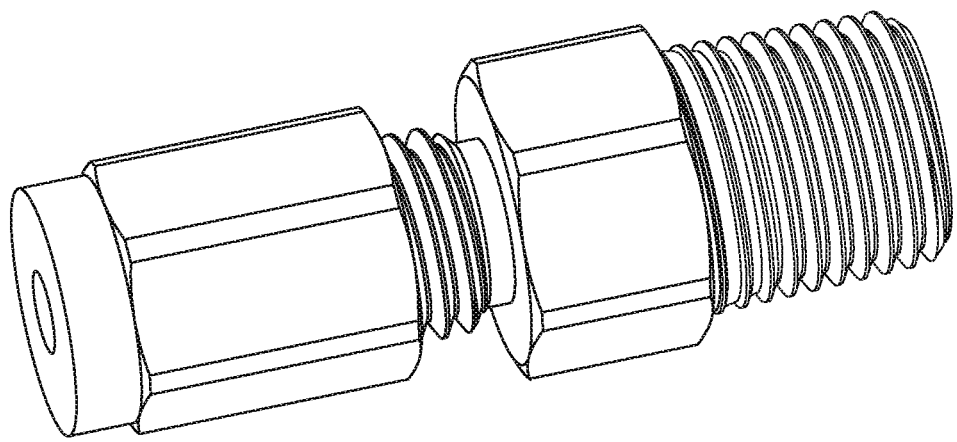
FIG. 7 is a perspective view of a component of a delivery system in accordance with the principles of the present disclosure.
Figure 8:
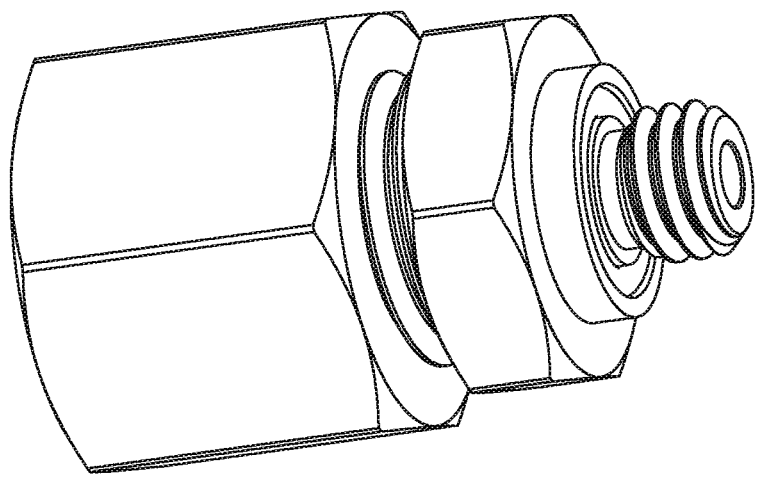
FIG. 8 is a perspective view of a component of a delivery system in accordance with the principles of the present disclosure.
Figure 9:
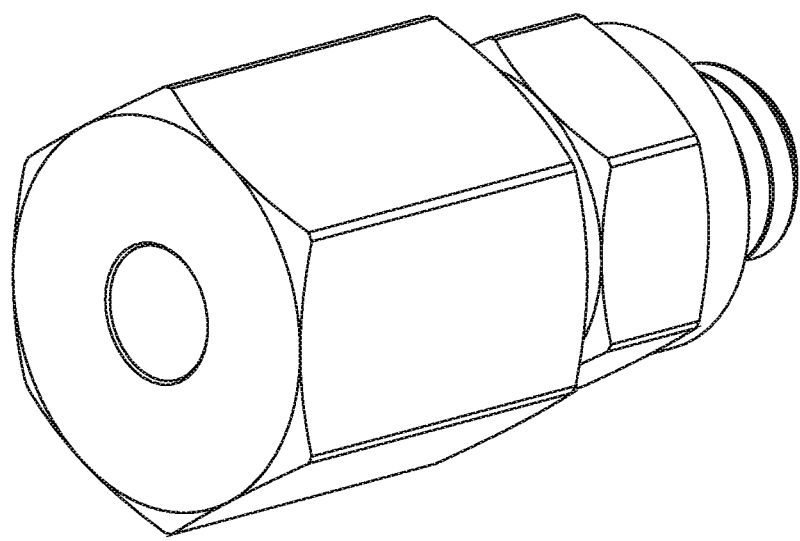
FIG. 9 is a perspective view of a component of a delivery system in accordance with the principles of the present disclosure.

Plunger seal 43 is configured to translate within chamber 24 and contact the fluid within chamber 24. Plunger 40 translates relative to body 14 between an initial orientation and a fully or entirely expelled orientation. In the initial orientation, plunger 40 is disposed adjacent the fluid within chamber 24. Plunger 40 translates such that plunger seal 43 applies a force to the second material. The force applied by plunger seal 43 causes the second material to be moved through an opening 60. In some embodiments, opening 60 is disposed coaxial relative to axis X1. In some embodiments, as shown in FIGS. 4 and 5, opening 60 is disposed perpendicular to axis X1. Compression of the fluid within chamber 24 causes the second material to flow from chamber 24 through opening 60. Movement of the fluid from chamber 24 causes a plunger in bone filling dispenser 100 to be actuated, as described herein.

Figure 10:
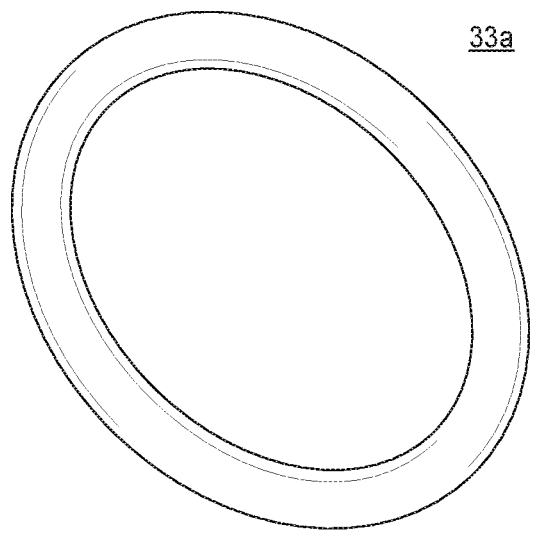
FIG. 10 is a perspective view of a component of a delivery system in accordance with the principles of the present disclosure.
Figure 11:
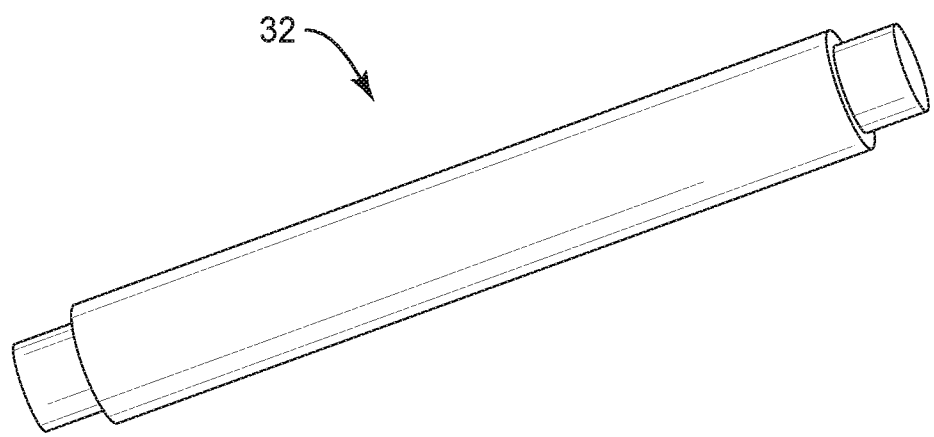
FIG. 11 is a perspective view of a component of a delivery system in accordance with the principles of the present disclosure.
Figure 12:
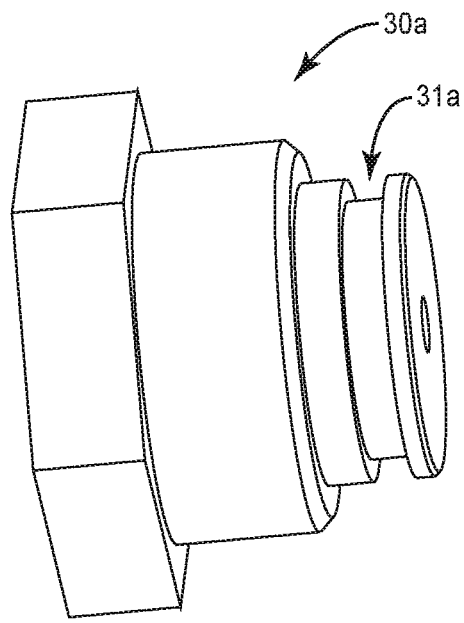
FIG. 12 is a perspective view of a component of a delivery system in accordance with the principles of the present disclosure.
Figure 13:
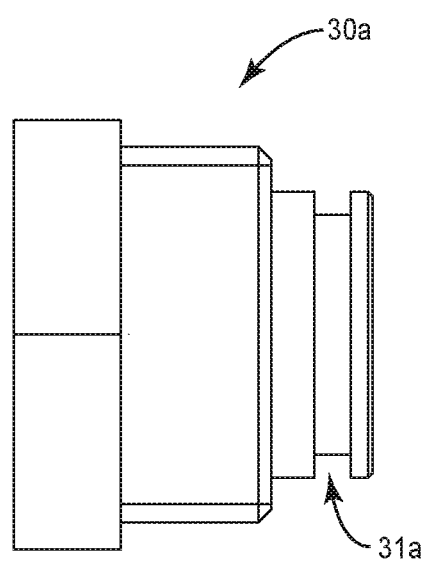
FIG. 13 is a perspective view of a component of a delivery system in accordance with the principles of the present disclosure.
Figure 14:
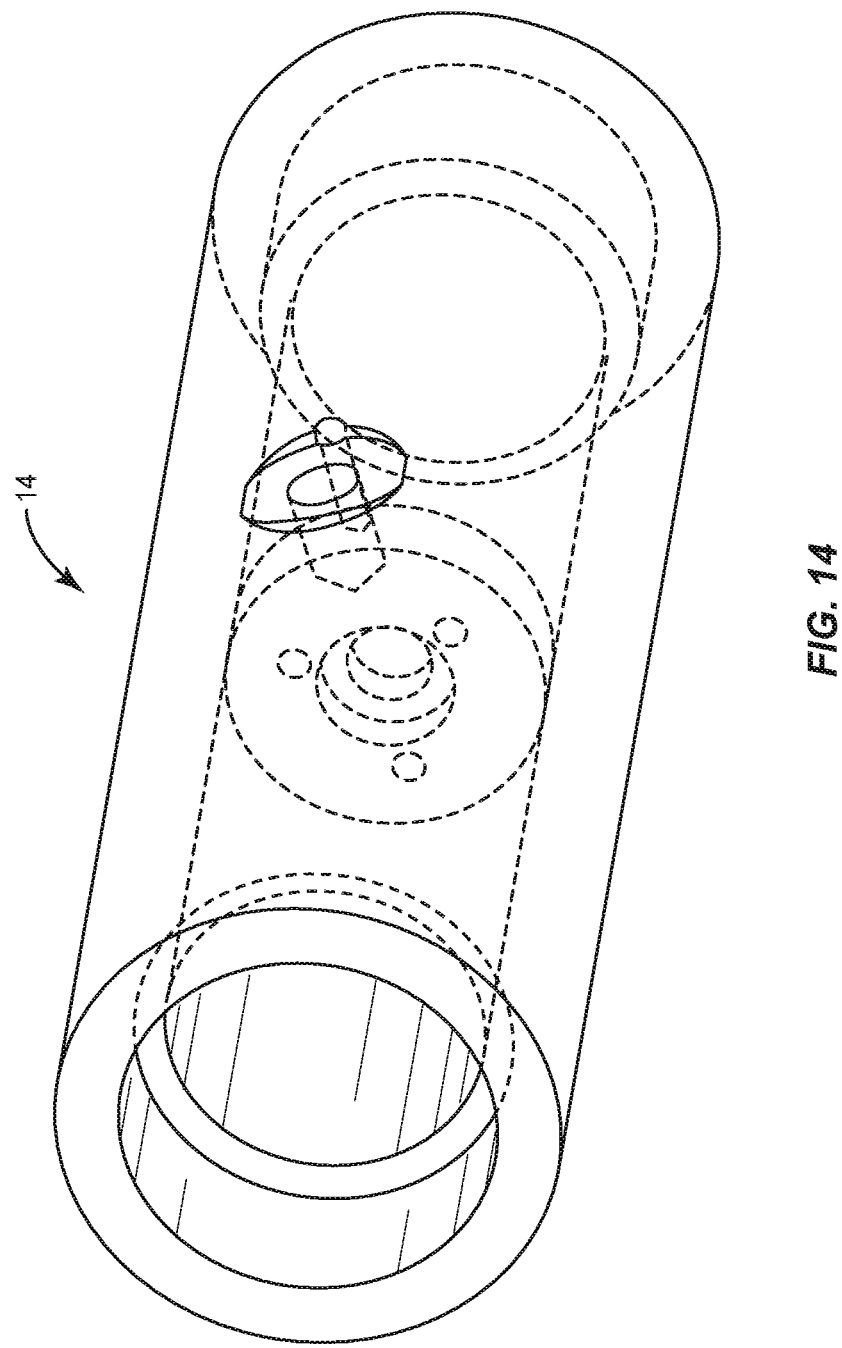
FIG. 14 is a perspective view of a component of a delivery system in accordance with the principles of the present disclosure.
Figure 15:
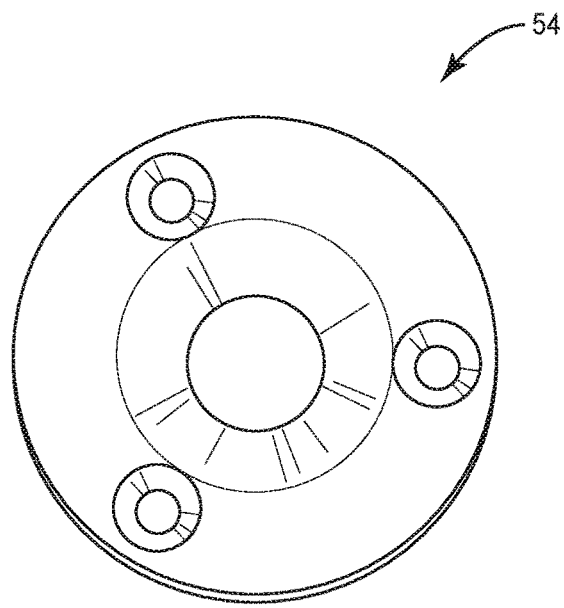
FIG. 15 is a perspective view of a component of a delivery system in accordance with the principles of the present disclosure.
Figure 16:
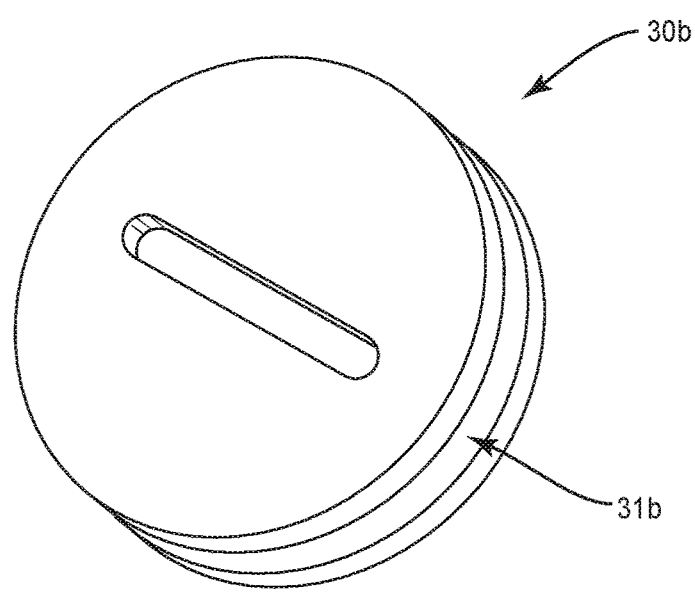
FIG. 16 is a perspective view of a component of a delivery system in accordance with the principles of the present disclosure.
Figure 17:
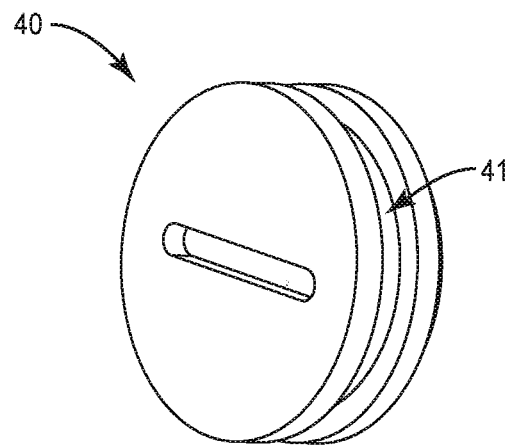
FIG. 17 is a perspective view of a component of a delivery system in accordance with the principles of the present disclosure.
Figure 18:
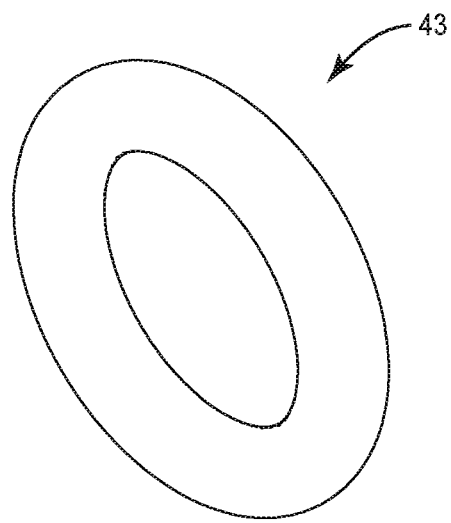
FIG. 18 is a perspective view of a component of a delivery system in accordance with the principles of the present disclosure.
Figure 19:
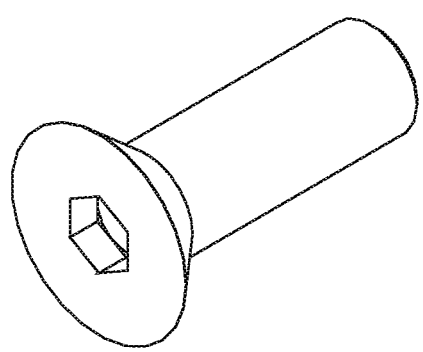
FIG. 19 is a perspective view of a component of a delivery system in accordance with the principles of the present disclosure.

In some embodiments, plunger 40 includes a slot configured for engagement with an instrument, such as, for example, a driver. In some embodiments, chamber 24 includes an air vent configured to facilitate translation of plunger 40 upon actuation by plunger 30. In some embodiments, plunger seals 33a, 33b, 43 include O-rings, as shown in FIGS. 10 and 18. In some embodiments, chamber 22 includes a smaller volumetric capacity than chamber 24 due to the plunger shaft extending therethrough. In some embodiments, chamber 24 includes a smaller diameter than chamber 22 to account for the volumetric difference. In some embodiments, system 10 includes a pressure relief valve. In some embodiments, system 10 is provided sterilized. In some embodiments, system 10 is provided as a sterilized kit including bone filler dispenser 100.

In some embodiments, opening 50 includes a port 52 having a taper, nozzle, valve and/or luer lock connection for connecting with the tubing. In some embodiments, opening 50 includes a pressure fit, friction fit or threaded connection for connecting with the tubing. In some embodiments, opening 50 is integrally connected or monolithically formed with the tubing. In some embodiments, the tubing includes ¾ inch tubing. In some embodiments, opening 60 includes a port 62 having a taper, nozzle, valve and/or luer lock connection for connecting with the tubing. In some embodiments, opening 60 includes a pressure fit, friction fit or threaded connection for connecting with the tubing. In some embodiments, opening 60 is integrally connected or monolithically formed with the tubing. In some embodiments, the tubing includes ¾ inch tubing. In some embodiments, the tubing has a length sufficient such to position the syringe out of a field of radiation.

In some embodiments, the tubing attached with opening 50 directs the fluid in chamber 22 to drive a plunger 102 within a barrel 104 of bone filler dispenser 100, as shown in FIG. 5. In some embodiments, opening 60 directs the fluid in chamber 24 to drive a plunger 106 in a barrel 108 of bone filler dispenser 100, as shown in FIG. 5. Bone filler dispenser 100 includes a dual barrel chamber dispenser oriented in a parallel configuration. Connection of bone filler dispenser 100 with cylinder 12 is configured to facilitate movement and/or translation of viscous material disposed within barrels 104, 108. The fluid expelled form cylinder 12 drives plungers 102, 106 disposed at an equal rate, such as, for example, a 1:1 ratio to simultaneous dispense the bone filling material in a static mixer. In some embodiments, chambers 22, 24 can be altered, such as, for example, by diameter and/or volumetric capacity to alter the rate of translation of the plungers, such as, for example, a 2:1 ratio. In some embodiments, barrels 104, 108 include different materials configured to be mixed before administering to a surgical site. In some embodiments, bone filler dispenser 100 includes a single plunger and the fluid from chambers 22, 24 applies a force to a surface of the single plunger to double the pressure applied to expel the bone fill material.

In some embodiments, a static mixer 120 is attached to an end of bone filler dispenser 100. In some embodiments, static mixer 120 includes a mixing element, such as, for example, a helical blade 122 configured to mix the materials, such as, for example, a first material and a second material within barrels 104, 108, respectively. At the point of entry of the first material is expelled from barrel 104 and the second material is expelled from barrel 108 onto an end of blade 122. Blade 122 is configured to receive the first material on one side of the helix and the second material on a second side of the helix. As the materials flow over blade 122, the first and second materials mix along the length of blade 122 within the static mixer.

In assembly, operation and use, system 10 is employed with a surgical procedure, such as, for a treatment of bone injuries, to provide bone repairs, to strengthen or rebuild bones, etc. In some embodiments, one or all of the components of system 10 can be delivered or implanted as a pre-assembled device or can be assembled in situ. System 10 may be completely or partially revised, removed or replaced.

For example, as shown in FIGS. 1-19, system 10 and accessories thereof, described above, can be employed during a surgical procedure for mixing and dispensing bone cement. In use, a medical practitioner obtains access to a surgical site including a bone in any appropriate manner, such as through incision and retraction of tissues. In some embodiments, system 10 can be used in any existing surgical method or technique including open surgery, mini-open surgery, minimally invasive surgery and percutaneous surgical implantation, whereby the bone is accessed through a mini-incision, or sleeve that provides a protected passageway to the area. Once access to the surgical site is obtained, the particular surgical procedure can be performed for treating or repairing the bone.

An incision is made in the body of a patient and a cutting instrument (not shown) creates a surgical pathway for implantation of components of system 10. A preparation instrument (not shown) can be employed to prepare tissue surfaces of the bone, as well as for aspiration and irrigation of a surgical region according to the requirements of a particular surgical application.

A material, such as, for example, pressurized air or a hydraulic fluid is injected into port such that the material moves through lumen 37 and into channel 35. As the material moves through lumen 37, the material causes second part 30b to translate relative to first part 30a along axis X1 in the direction shown by the arrows in FIG. 2. Translation of second part 30b relative to first part 30a along axis X1 causes the pneumatic material within chamber 22 to move through opening 50 and causes shaft 32 to translate plunger 40 relative to body 14 in the direction shown by the arrows in FIG. 2 such that plunger 40 moves the second material in chamber 24 through opening 50 and port 52. The pneumatic material moves out of opening 50 and into the tubing attached with opening 50 such that the pneumatic material drives plunger 102 to move a component of a bone cement within barrel 104 of bone filler dispenser 100 into static mixer 120. The second material simultaneously moves out of opening 50 and port 52 and tubing attached with port 52 into static mixer 120. The pneumatic material moves out of opening 50 and into the tubing attached with opening 50 at the same time the second material moves out of opening 50 and port 52 and tubing attached with port 52 to drives plungers 102, 106 at an equal rate, such as, for example, a 1:1 ratio to simultaneously move the first and second components of the bone cement into static mixer 120. Plungers 102, 106 create a force that moves the first and second components of the bone cement through static mixer 120 such that the first and second components of the bone cement become mixed within static mixer 120 and the mixed first and second components of the bone cement exit static mixer through an opening in static mixer for delivery of the mixed bone cement to a target location or area, such as, for example, holes, fractures, voids and/or depressions in the bone such that the mixed bone cement fills all or at least a portion of the holes, fractures, voids and/or depressions to maintain or improve the bone's structural integrity. Components of system 10, e.g., a needle attached to bone filler dispenser 100 is delivered to the surgical site along the surgical pathway(s) and into or onto bone tissue.

In one embodiment, system 10 may also deliver an agent, which may be mixed in the bone cement or delivered separately from the bone cement. In some embodiments, the bone cement may be a bone filler material that includes, for example, bone material including autograft, allograft, xenograft, MASTERGRAFT®, collagen or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, TCP, HA-TCP, calcium sulfate, or other resorbable polymers such as polylactide, polyglycolide, polytyrosine carbonate, polycaprolactone and their combinations.

In some embodiments, the agent may include therapeutic polynucleotides or polypeptides. In some embodiments, the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of correction system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair bone deterioration or damage, with the aid of the system 10. Upon completion of the procedure, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A device comprising:
   a body extending along a longitudinal axis between opposite proximal and distal ends, the body comprising a proximal chamber, a distal chamber and a wall between the chambers, the body including a first port in communication with the proximal chamber and a second port in communication with the distal chamber; and
   a shaft movably positioned within the body, the shaft extending through the wall and comprising a proximal plunger positioned within the proximal chamber and a distal plunger positioned within the distal chamber,
   wherein pressure introduced through an opening in the proximal end moves the shaft such that the proximal plunger moves a fluid within the proximal chamber out of the first port and the distal plunger moves a fluid within the distal chamber out of the second port to simultaneously actuate a bone filler dispenser.

2. A device as recited in claim 1, wherein the chambers are coaxial with the longitudinal axis.

3. A device as recited in claim 1, wherein the proximal plunger and the distal plunger actuate plungers of the bone filler dispenser at an equal rate to expel bone filler material from the bone filler dispenser.

4. A device as recited in claim 1, wherein the fluid actuates a first material and a second material from the bone filler dispenser at a 1:1 ratio.

5. A device as recited in claim 1, wherein the plungers are fixed to the shaft.

6. A device as recited in claim 1, wherein the first port and the second port extend transverse to the longitudinal axis.

7. A device as recited in claim 1, wherein the second port is coaxial with the longitudinal axis.

8. A system comprising:
   a dispenser comprising:
      a body extending along a longitudinal axis between opposite proximal and distal ends, the body comprising a proximal chamber, a distal chamber and a wall between the chambers, the body including a first port in communication with the proximal chamber and a second port in communication with the distal chamber, and a shaft movably positioned within the body, the shaft extending through the wall and comprising a proximal plunger positioned within the proximal chamber and a distal plunger positioned within the distal chamber;

a delivery device coupled to the proximal end;

a bone filler dispenser coupled to the dispenser; and a mixing device coupled to the bone filler dispenser, wherein pressure from the delivery device is introduced through an opening in the proximal end to move the shaft such that the proximal plunger moves a fluid within the proximal chamber out of the first port and the distal plunger moves a fluid within the distal chamber out of the second port to simultaneously actuate the bone filler dispenser such that materials within the bone filler dispenser move into the mixing device.

9. A system as recited in claim 8, wherein:

the bone filler dispenser comprises a third port that is connected to the first port by tubing and a fourth port that is connected to the second port by tubing, the third port being in communication with a first barrel of the bone filler dispenser, the fourth port being in communication with a second barrel of the bone filler dispenser, the first barrel comprising a first plunger movably disposed therein and the second barrel comprising a second plunger movably disposed therein; and the fluids move out of the first and second ports and into the barrels to move the first and second plungers relative to a body of the bone filler dispenser such that the first plunger moves a first material out of the first barrel and into the mixing device and the second plunger moves a second material out of the second barrel and into the mixing device.

10. A system as recited in claim 9, wherein the first material is a first component of a bone cement and the second material is a second component of the bone cement.

11. A system as recited in claim 9, wherein the first barrel is spaced apart from the second barrel by a wall of the bone filler dispenser such that the first and second materials do not come into contact with one another until the first and second materials are disposed in the mixing device.

12. A system as recited in claim 9, wherein the fluids move out of the first and second ports and into the barrels at a 1:1 ratio.

13. A system as recited in claim 9, wherein the first and second plungers create pressure that moves the first and second materials through the mixing device to mix the first and second materials within the mixing device and expel the mixed first and second materials from an opening in the mixing device.

14. A system as recited in claim 10, wherein the mixing device is a static mixer comprising a helical blade that mixes the first and second materials as the first and second materials move along a length of the helical blade.

15. A system as recited in claim 8, wherein the delivery device is an inflation syringe.

16. A system as recited in claim 8, wherein the fluids are pastes.

17. A method of mixing cement, comprising:

introducing pressure from a delivery device through an opening in a proximal end of a body of a dispenser such that the pressure moves a shaft of the dispenser along a longitudinal axis defined by the dispenser, the shaft comprising a proximal plunger positioned in a proximal chamber of the body and a distal plunger positioned in a distal chamber of the body, translation of the shaft moves the proximal plunger to push a fluid within the proximal chamber out of a first port of the body and moves the distal plunger to push a fluid within the distal chamber out of a second port of the body to simultaneously actuate a bone filler dispenser.

18. A method of mixing cement as recited in claim 17, wherein the bone filler dispenser includes first and second plungers that are actuated at an equal rate by the proximal and distal plungers.

19. A method of mixing cement as recited in claim 18, wherein the first plunger is disposed in a first barrel of the bone filler dispenser and the second plunger is disposed in a second barrel of the bone filler dispenser, the first plunger moving a first component of a bone cement in the first barrel from the first barrel and into a mixing device and the second plunger moving a second component of the bone cement in the second barrel from the second barrel and into the mixing device.

20. A method of mixing cement as recited in claim 17, wherein the fluids are pneumatic fluids.

* * * * *

UNITED STATES PATENT AND TRADEMARK OFFICE
CERTIFICATE OF CORRECTION

PATENT NO.        : 10,357,300 B2
APPLICATION NO.   : 15/612063
DATED             : July 23, 2019
INVENTOR(S)       : Sasaki et al.

Page 1 of 1

It is certified that error appears in the above-identified patent and that said Letters Patent is hereby corrected as shown below:

In the Specification

In Column 6, Line 13, delete "barrel 14" and insert -- barrel 104 --, therefor.

Signed and Sealed this
Eighteenth Day of February, 2020

Andrei Iancu
*Director of the United States Patent and Trademark Office*